US00PP20588P3

(12) United States Plant Patent
Dozier, Jr. et al.

(10) Patent No.: US PP20,588 P3
(45) Date of Patent: Dec. 22, 2009

(54) CHESTNUT PLANT NAMED 'AU BUCK I'

(50) Latin Name: *Castanea mollissina Blume*
Varietal Denomination: Au Buck I

(75) Inventors: W. Alfred Dozier, Jr., Opelika, AL (US); Joseph Daniel Norton, Auburn, AL (US); Curtis J. Hansen, Opelika, AL (US)

(73) Assignee: Auburn University, Auburn, IL (US)

( * ) Notice: Subject to any disclaimer, the term of this patent is extended or adjusted under 35 U.S.C. 154(b) by 0 days.

(21) Appl. No.: 12/012,091

(22) Filed: Jan. 30, 2008

(65) Prior Publication Data

US 2009/0193550 P1 Jul. 30, 2009

(51) Int. Cl.
*A01H 5/00* (2006.01)

(52) U.S. Cl. ..... Plt./152
(58) Field of Classification Search ..... Plt./152
See application file for complete search history.

(56) References Cited

PUBLICATIONS

Lin ye ji et al., "Forest Science & Technology", Jan. 1989, pp. 16–18, Baker Auxiliary Stacks SD1 SDI, L56, No. 2–1990.

Crane, H.L. et al., Nut Breeding', U.S. Dept. of Agriculture Yearbook, Jan. 1937, pp. 827–837.

Hemming, E. Sam, "Chinese Chestnut in Maryland", Jan. 1944, pp. 32–34, A.R. Northern Growers Assoc.

Kim, Kap Duk et al., Studies on the Farmers Cultivating Chestnut Orchards in Korea and Its Financial Analysis,Jan. 1971, pp. 51–74, Bull. Seol. Nut. Univ. Fores., No. 8.

Snare Lester, Chestnuts Production', Jan. 1996, pp. 422–427, NSW Agriculture, Agfact H3.1.50., hhtp://www.r-irdc.gov.au/pub/handbook/chestnuts.pdf.

Harris, Hubert et al., Three Chinese Chestnuts: Au–Cropper, Au–Leadder, And Au–Homestead–Their History And Production, Mar. 1980, pp. 3–8, Agricultural Experiment Station Auburn University Circular 247.

Jaynes, Richard A. et al., "Handbook of North American Nut Trees", pp. 264–286, The W.F. Humphrey Press, Inc. New York.

*Primary Examiner*—Annette H Para
(74) *Attorney, Agent, or Firm*—Haverstock & Owens LLP

(57) ABSTRACT

'AU Buck I' is a new and distinct Chinese chestnut cultivar that is precocious, produces a large crop annually of small to medium sized nuts that mature early and the nuts start dropping about August 28. Nut drop continues for a 4–5 week period. The nuts mature and start dropping 3–4 weeks before most cultivars. The early nut drop and small to medium nut size of 'AU Buck I' make it ideal for use as a food source for wildlife. 'AU Buck I' is a medium to tall tree with a height of 8.53 meters and a smaller canopy area (62.74 square feet) than most Chinese chestnut trees. 'AU Buck I' is the first cultivar to mature and drop nuts in a series of four Chinese chestnut cultivars that will provide for a continuous nut drop of a high energy wildlife food source from late August through mid-to-late November.

3 Drawing Sheets

Latin name of the genus and species of the plant claimed: *Castanea mollissima* Blume.
Variety denomination: 'AU Buck I'.

BACKGROUND OF THE INVENTION

A Chinese chestnut planting was established at Auburn University, Auburn, Ala., from nuts collected in China. The planting was established on the United States Department of Agriculture Horticulture Farm which in later years became the Mainstation Horticulture Farm. Precocious and prolific-bearing, blight resistant seedlings were selected for nut appearance, size and quality. Each generation of seedlings were the product of controlled mass pollination from the most promising seedlings selected from the previous generation. 'AU Cropper', 'AU Leader' and 'AU Homestead' were released from a second generation of approximately 2000 seedlings. A planting of third generation seedlings from controlled mass pollination of 'AU Leader', 'AU Homestead' and 'AU Cropper' was established at the Auburn University Piedmont Substation at Camp Hill, Ala.

SUMMARY OF THE INVENTION

'AU Buck I' is an open pollinated seedling of 'AU Cropper'.

The present invention relates to a new and distinct Chinese chestnut cultivar that is blight resistant, precocious, produces a heavy crop annually, produces small to medium sized nuts (9.3 g) and begins nut drop about August 28 and continues for a 4–5 week period. The nuts mature and start dropping 3–4 weeks earlier than most chestnut cultivars. The large crop of small to medium sized nuts is an excellent food source for wildlife such as deer, turkey and squirrel. The 15-year old 'AU Buck I' tree is a medium-sized tree that is 8.53 meters tall with a canopy width of 8.94 meters and a canopy area of 62.74 square meters. The 'AU Buck I' tree produced nuts the third year after transplanting, has produced a heavy crop annually, and produced 66.5 kg (146.5 lbs) of nuts in 2006. There has been no evidence of insect or disease damage to the tree, foliage, or nuts. 'AU Buck I' is the first cultivar to mature and drop nuts in a series of four Chinese chestnut cultivars that will provide a continuous nut drop of a high energy wildlife food source from late August through mid-to-late November. 'AU Buck II', 'AU Buck III' and 'AU Buck IV' are the other three cultivars, which are disclosed in U.S. patent application Ser. No. 12/012,025, filed on Jan. 30, 2008, and entitled "CHESTNUT PLANT NAMED 'AU BUCK II'", U.S. patent application Ser. No.

12/012,110, filed on Jan. 30, 2008, and entitled "CHESTNUT PLANT NAMED 'AU BUCK III'" and U.S. patent application Ser. No. 12/012,112, filed on Jan. 30, 2008, and entitled "CHESTNUT PLANT NAMED 'AU BUCK IV'", which are hereby incorporated by reference.

The new cultivar is able to be asexually reproduced by budding or grafting onto a seedling Chinese chestnut rootstock. The unique characteristics come true to form and are established and transmitted through asexual propagation.

DETAILED BOTANICAL DESCRIPTION

Figure 1:
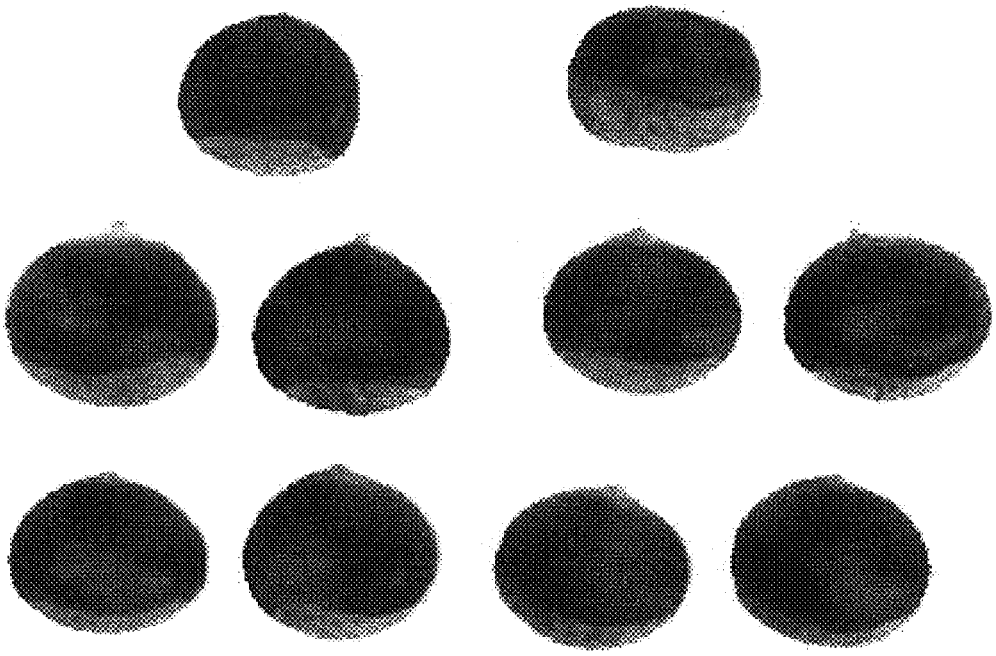
FIG. 1 is a photograph of nuts of the 'AU Buck I' cultivar.
Figure 2:
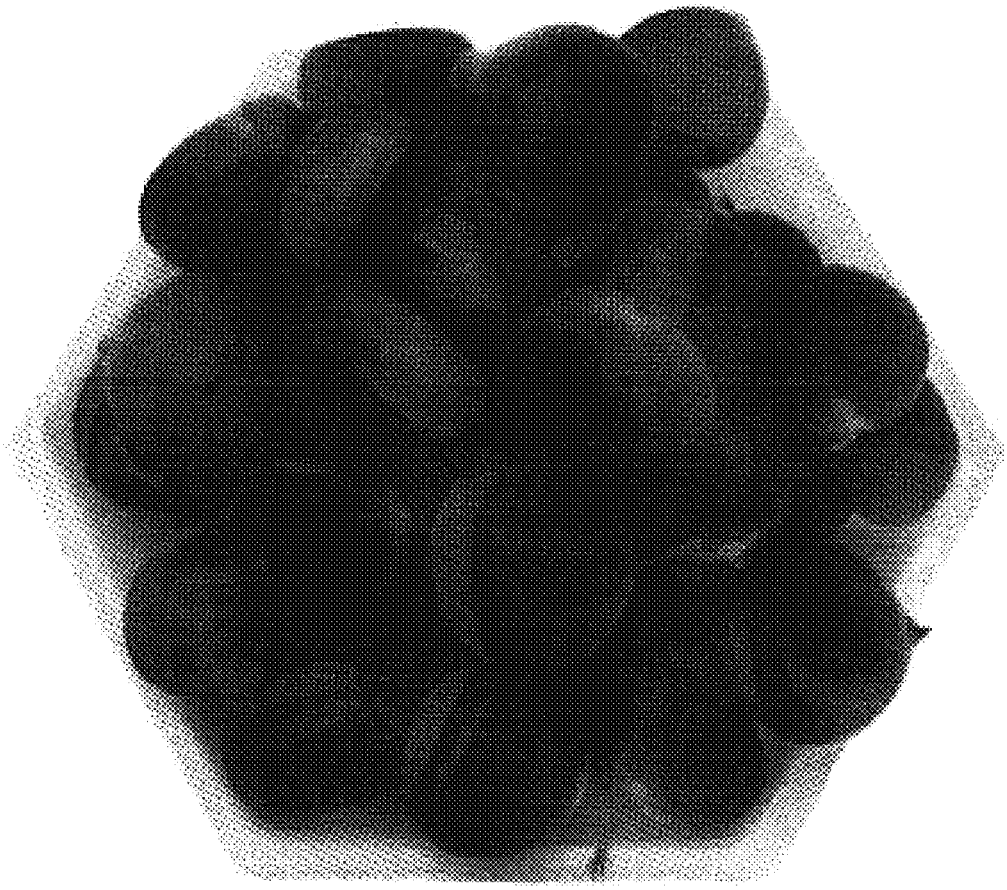
FIG. 2 is a photograph of nuts of the 'AU Buck I' cultivar.
Figure 3:
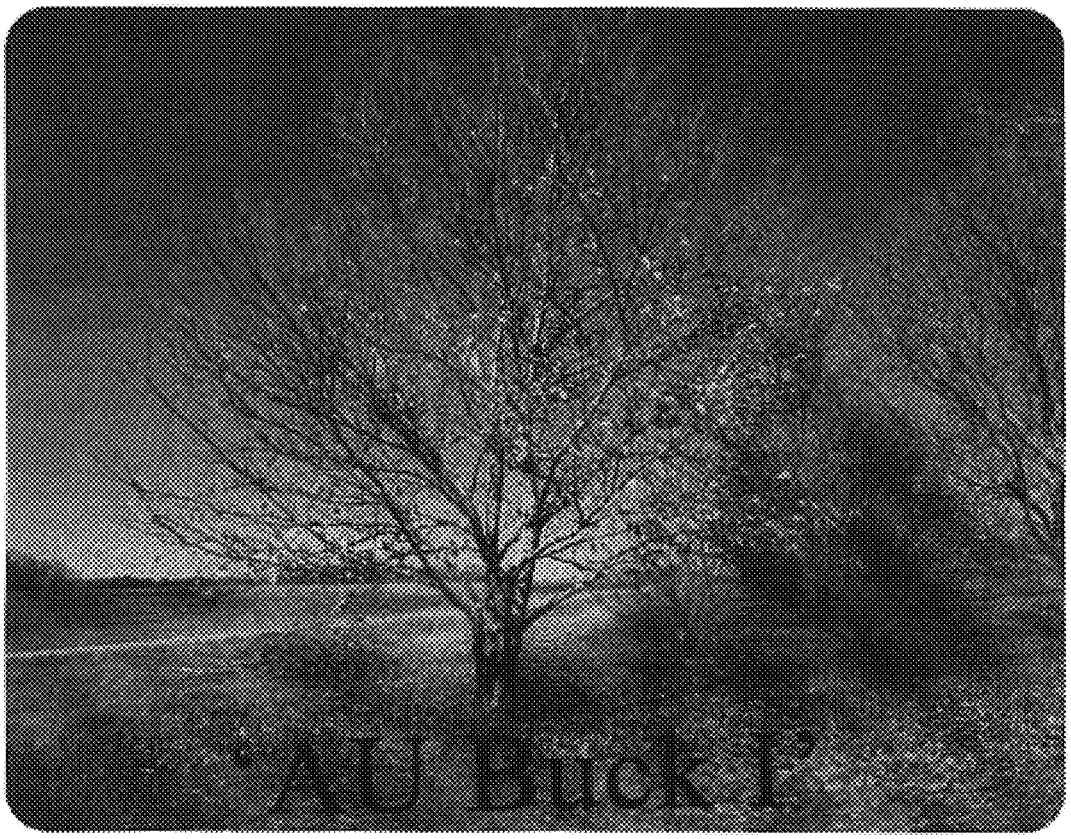
FIG. 3 is a photograph of a tree of the 'AU Buck I' cultivar.

The Chinese chestnut, *Castanea mollissima* Blume, is a cold, hardy, temperate zone species native to China. It can be grown between 30° and 50° latitudes. The Chinese chestnut is resistant to chestnut blight fungus *Cryphonectria parasitica*. Generally, Chinese chestnuts are grown on a wide range of soils, but well-drained, deep and fertile soils are considered the best. Soils should be slightly acidic with pH 5.6–6.5. The name *mollissima* means soft hair and this species is recognized by dense hair on young leaves and downy yellow terminal parts of the shoots in winter. The leaf blade is thicker and, in general, mature leaves are broader than those of other species. The nuts have a small scar or hilum. The pellicle or thin membranous skin on the nuts is thin and peels readily from the kernel. The trees are a spreading type and long-lived with a round top. The trees have bark with furrows and buds with 3–4 scales and leaves are 2 ranked, serrated with numerous parallel veins.

Chestnuts are monoecious and staminate flowers appear on erect cylindrical catkins with 10–20 stamens and 6-parted calyx. Pistillate flowers are borne on lower part of the upper staminate catkins and rarely on separate catkins, usually 3 in a prickly symmetrical involucre with 7–9 styles and a 6-celled ovary. Nuts are small, brown with a pale scar at the base. Generally, 1–3 nuts per involucre or bur are present.

'AU Buck I' is a medium tall tree that has a broadly oval shape and low, dense, and spreading branches. The original 15-year old tree of 'AU Buck I' is 8.53 meters (28 feet) tall with a trunk diameter at breast height of 25.4 cm (10.0 inches). The canopy is 8.94 meters (29.31 feet) wide and covers an area of 62.74 square meters (638 square feet). The average nut length is 26.1 mm (1.03 inches) and the average nut width is 30.4 mm (1.20 inches). The nuts start dropping about August 28 and continue to drop for 4–5 weeks. The tree is very prolific, fruits annually, and starts dropping nuts about 3–4 weeks before most cultivars.

In the planting at the Piedmont Substation, Camp Hill, Ala., accurate yields could not be obtained due to extremely heavy wildlife (deer and turkey) feeding. Therefore, the trees were rated for crop load each year. 'AU Buck I' has been rated with a large crop load each season. In the fall of 2006, individual trees were caged with 6 foot (1.83 meters) tall chicken wire prior to nut drop to exclude wildlife, and nuts were picked up daily during nut drop. The original 15-year old tree of 'AU Buck I' produced 66.5 kg (146.5 pounds) of nuts in 2006. This yield is above the reported yields for similar-aged trees.

The table below illustrates the specific differences between the 'AU Buck I' cultivar and the 'Revival' cultivar.

The botanical details of this new and distinctive variety of chestnut tree - with color definitions (except those in common color terms) referenced to Royal Horticultural Society's Colour Chart (RHS) and color was also determined using an electronic spectrophotometer to determine hue angle and Chroma (spectrophotometer model CM-2002; Minolta Camera Co., Japan).
'AU BUCK I' CHESTNUT Tree:

Size (at maturity) - small - fifteen year old original tree is 8.53 meters tall with a canopy width of 8.94 meters and a canopy area of 62.74 sq. meters
Tree shape is broadly oval with dense, low and spreading branches.
Vigor - very vigorous Trunk:

Form - upright, spreading with branches low and dense
Texture - relatively smooth
Color of bark - grey-brown RHS N199A, Chroma C* 15.89, hue angle 91.08

Branches:

Form - spreading
Texture - relatively smooth
Lenticels - few, small
Branching habit - dense, low and spreading
Color - new wood: grey-brown, RHS N199B, Chroma C* 14.72, hue angle 79.23, mature wood: grey-brown, RHS N199B Chroma C* 14.02, hue angle 93.86

Foliage:

Quantity - abundant
Density - dense

Leaves:

Size - large. Length (cm) 17.1 (14.1-23.1) [20]
width (cm) 7.5 (5.8-9.2) [20]
leaf ratio 2.3 (1.9-2.7) [20]
Shape - elliptic to ovate
leaf tip - acute to acuminate
leaf base - rounded; oblique
Thickness - thick. Leaf venation 1° pinnate: 2° ± parallel, prominent abaxially
Texture - coriaceous (thick)
Margin - serrate; with small to medium teeth, spreading
Petiole - length 1.0 cm (0.7-1.3) [20]
Petiole pubescence - glabrous to sparsely hairy
Color- adaxial surface, glabrous blade; glabrous veins, rarely with sparse simple hairs, dark green; shiny, RHS 147A, Chroma C* 12.32, hue angle 122.62
abaxial surface, moderately hairy, stellate hairs on blade, glabrous veins, RHS 148B, Chroma C* 19.97, hue angle 109.24

Bloom:

Amount of bloom - heavy
Color - at anthesis, 161D greyed-yellow group, 157D green-white group, 155C white group
Blooming period - mid-May. After foliation in April.
Age at which tree starts flowering - early, 2-3 years after graft replacement.
Male flower - Catkin length (cm) - 14.8 (11.4-17.5) [3]
Male flower - stamen number per catkin - 11.1 (10-12) [10]
Female flower - flower number per bur - 3
Female flower - style number per flower 8 (7-9) [3]

Crop:

Bearing - regular annual bearer
Productivity - prolific
Ripening period - long, nuts begins dropping August 28 and continues for a 4-5 week period.
Distribution of nuts on tree - well distributed, fruits on terminals with 2-4 burs per terminal.
Tenacity - burs crack while on tree and nuts release and drop from bur.

Hull:

Description - spiny round bur
Size - 1.99-2.32" in diameter

-continued

Number of nuts - 2-3 per bur
Dehiscence - splits easily when still on tree
Color - yellow-green at dehiscence, RHS N144C
Nut:

Size - medium; average size - 1.03" × 1.22" × 0.67". Average weight - 9.3 grams - 49 (46-54) nuts per pound.
Form - flattened on 1 side, hemispheric on other side; basal end nearly flat to broadly rounded; apex broadly rounded with a small tip
Blossom end - small pointed tip
Basal end - flattened
Color - dark brown, lustrous; RHS 200B, Chroma C* 12.34, hue angle 42.90
Pubescence- long and short hairs, simple, fine and white restricted to the distal ⅛ end of the nut, sparse, glabrate to glabrous elsewhere
Shell - thin
Hardness of shell - relatively hard, yet not rigid
Texture of shell - smooth
Percentage of kernel to nut - very high-90-95%
Kernel:

Size - almost as large as nut size
Form - same as nut shape
Pellicle - thin
Flavor - excellent, very sweet
Color - light straw color, RHS 162A, Chroma C* 48.81, hue angle 82.35
Resistance to insects: no unusual susceptibilities noted
Resistance to disease: no susceptibilities to disease noted
The chestnut tree and its nuts herein described may vary in slight detail due to climatic and soil conditions under which the variety may be grown; the present description being of the variety as grown in Camp Hill, Ala.

The botanical details of this variety of chestnut tree - with color definitions (except those in common color terms) referenced to Maerz and Paul Dictionary of Color - are as follows:
'REVIVAL'

Tree:

Size (at maturity) - large
Vigor - very vigorous
Trunk:

Form - upright with branches spreading in upper reaches of tree
Texture - relatively smooth
Color of bark - Silvergray (13-A-1)
Branches:

Form - strong
Texture - relatively smooth
Lenticels - few, small
Branching habit - spreading in upper region of tree
Color - new wood: reddish brown and glossy, mature wood: silver gray
Foliage:

Quantity - abundant
Density - dense
Leaves:

Size - large. Average length - 5-7" (including petiole).
Average width - 2"
Shape - oblong with acute tip and rounded base
Thickness - thick
Texture - smooth
Margin - dentate
Petiole - length: medium. Thickness: medium.
Color - Top tide - glossy dark green (22-L-12).
Under side - lighter green (21-D-7).
Bloom:

Amount of bloom - heavy
Color- cream white (17-B-1)
Blooming period - late. After leaf out in April -continued Age at which tree starts flowering - early; 2-3 years years after graft replacement.
Crop:

Bearing - regular (yearly) bearer
Productivity - prolific
Ripening period - short. September 15-October 1.
Distribution of nuts on tree - well distributed
Tenacity - burrs crack while on tree and nuts easily release, many falling by themselves
Hull:

Description - spiny, round burr
Size - 3-4" in diameter
Number of nuts - 2-3 per burr
Dehiscence - splits easily when still on tree. Some entire burrs split and fall to ground
Color - brown (15-A-8)
Nut:

Size - large. Average size - 1⅛" × 1⅛" × 1" thick.
Average weight - 24-32 nuts per pound
Form - broad and ovoid on one side, flat on other side
Blossom end - pointed tip
Basal end - flattened
Color - India Red (7-1.-6).
Shell - thin
Hardness of shell - relatively hard, yet not rigid
Texture of shell - smooth
Percentage of kernel to nut - very high (95%)
Kernel:

Size - almost as large as nut size
Form - same as nut shape
Pellicle - thin
Flavor - excellent, very sweet.
Color - Oyster white (10-B-1)
Resistance to insects: no unusual susceptibilities noted
Resistance to disease: very high inherent resistance to chestnut bark fungus (*Endothia parasitica*), no other susceptibilities to any other disease
The chestnut tree and its nuts herein described may vary in slight detail due to climatic and soil conditions under which the variety may be grown; the present description being of the variety as grown in Alachua, Fla.

'AU Buck I' is different from 'AU Gobbler I' in several ways. For example, the size of the trees, the trunk forms and colors, the branches, the leaves and the nuts have differences. Specifically, the 'AU Buck I' tree is shorter with a canopy width and canopy area much smaller than the 'AU Gobbler I' tree. The 'AU Buck I' branches are spreading, dense, low and grey-brown; whereas, the 'AU Gobbler I' branches are upright, high, diffuse and brown (new) or greyed-green (mature). The leaves differ in size, shape, texture, margin, petiole and color. The average weight of the nuts of 'AU Buck I' is 9.3 grams versus 7.7 grams for 'AU Gobbler I'. Furthermore, 'AU Buck I' has roughly 49 nuts per pound, and 'AU Gobbler I' has roughly 59 nuts per pound.

'AU Buck I' is different from 'AU Gobbler II' in several ways. For example, the trees, the trunk colors, the branch colors, the leaves, the crop and the nuts have differences. Specifically, the 'AU Buck I' tree is taller with a canopy width and canopy area smaller than the 'AU Gobbler II' tree. The 'AU Buck I' branches are grey-brown; whereas the 'AU Gobbler II' branches are brown (new) or greyed-green (mature). The leaves differ in size, shape, texture, margin and color. The ripening period for the 'AU Buck I' is around August 28 and continues for a 4–5 week period, but the 'AU Gobbler II' ripening period is around September 5 and continues for 4–5 weeks. The average weight of the nuts of 'AU Buck I' is 9.3 grams versus 5.7 grams for 'AU Gobbler II'. Furthermore, 'AU Buck I' has roughly 49 nuts per pound, and 'AU Gobbler II' has roughly 65–101 nuts per pound.

'AU Buck I' is different from 'AU Premier' in several ways. For example, the trees, the trunk colors, the branch colors, the leaves, the crop and the nuts have differences. Specifically, the 'AU Buck I' tree is taller with a canopy width and canopy area larger than the 'AU Premier' tree. The 'AU Buck I' has a grey-brown trunk, and the 'AU Premier' has a greyed-green trunk. The 'AU Buck I' branches are grey-brown; whereas, the 'AU Premier' branches are brown (new) or greyed-green (mature). The leaves differ in size, shape, thickness, texture, margin, petiole and color. The ripening period for the 'AU Buck I' is around August 28, but the 'AU Premier' ripening period is early September through mid-November. The average weight of the nuts of 'AU Buck I' is 9.3 grams versus 1.26 grams for 'AU Premier'. Furthermore, 'AU Buck I' has roughly 49 nuts per pound, and 'AU Premier' has roughly 360.3 nuts per pound.

'AU Buck I' is different from 'AU Encore' in several ways. For example, the trees, the trunk colors, the branch colors, the leaves, the crop and the nuts have differences. Specifically, the 'AU Buck I' tree is taller with a canopy width and canopy area larger than the 'AU Encore' tree. The 'AU Buck I' has a grey-brown trunk, and the 'AU Encore' has a greyed-green trunk. The 'AU Buck I' branches are grey-brown; whereas, the 'AU Encore' branches are brown (new) or greyed-green (mature). The leaves differ in size, shape, thickness, texture, margin, petiole and color. The ripening period for the 'AU Buck I' is around August 28, but the 'AU Encore' ripening period is late September through late November. The average weight of the nuts of 'AU Buck I' is 9.3 grams versus 2.4 grams for 'AU Encore'. Furthermore, 'AU Buck I' has roughly 49 nuts per pound, and 'AU Encore' has roughly 189.2 nuts per pound.

What is claimed is:

1. A new and distinct cultivar of the species *Castanea mollissima* Blume named 'AU Buck I' as described and illustrated herein.

* * * * *

'AU Buck I'

'AU Buck I'